United States Patent
Chung et al.

(10) Patent No.: US 10,959,600 B2
(45) Date of Patent: Mar. 30, 2021

(54) ENDOSCOPE DEVICE FOR DETECTING DISEASE BASED ON THERMAL IMAGES

(71) Applicant: GWANGJU INSTITUTE OF SCIENCE AND TECHNOLOGY, Gwangju (KR)

(72) Inventors: Eui Heon Chung, Gwangju (KR); Gyung Seok Oh, Gwangju (KR); Su Woong Yoo, Gwangju (KR); Soon Joo Hwang, Gwangju (KR)

(*) Notice: Subject to any disclaimer, the term of this patent is extended or adjusted under 35 U.S.C. 154(b) by 409 days.

(21) Appl. No.: 15/694,652

(22) Filed: Sep. 1, 2017

(65) Prior Publication Data
US 2018/0055335 A1 Mar. 1, 2018

(30) Foreign Application Priority Data
Sep. 1, 2016 (KR) .................. 10-2016-0112819

(51) Int. Cl.
*A61B 1/00* (2006.01)
*A61B 1/12* (2006.01)
(Continued)

(52) U.S. Cl.
CPC ............ *A61B 1/00009* (2013.01); *A61B 1/05* (2013.01); *A61B 1/0676* (2013.01); *A61B 1/128* (2013.01); *A61B 5/0084* (2013.01); *A61B 5/015* (2013.01)

(58) Field of Classification Search
CPC ....... A61B 1/0009; A61B 1/0676; A61B 1/05; A61B 1/128; A61B 1/04; A61B 5/015; A61B 5/0084; A61B 5/742; A61B 2017/00084; A61B 2017/00088; A61B 2017/00092; A61B 2017/00097; A61B 2017/00101; A61B 2018/00791; A61B 2018/00797; A61B 2018/00803;
(Continued)

(56) References Cited

U.S. PATENT DOCUMENTS 5,445,157 A * 8/1995 Adachi ................. A61B 1/05
                                                    600/109
5,999,843 A   12/1999 Anbar
(Continued)

FOREIGN PATENT DOCUMENTS

| JP | 2002512070 A | 4/2002 |
| JP | 2013515586 A | 5/2013 |
| KR | 20120078893 A | 7/2012 |

*Primary Examiner* — Pascal M Bui Pho
*Assistant Examiner* — Sean D Mattson
(74) *Attorney, Agent, or Firm* — Loza & Loza, LLP; Heidi L. Eisenhut

(57) ABSTRACT

Disclosed is an endoscope device. An endoscope device according to an embodiment of the present invention includes: a heating source that heats a diagnosis target tissue; a cooling source that cools the diagnosis target tissue; a sensing unit that measures temperature of the diagnosis target tissue; and an image processing unit that obtains a first value meaning a temperature change for a predetermined time of the diagnosis target tissue heated by the heating source on the basis of the temperature obtained by the sensing unit, obtains a second value meaning time until the heated diagnosis target tissue is stabilized by being cooled by the cooling source after obtaining the first value, and produces an image for diagnose a tumor in the diagnosis target tissue on the basis of the first value and the second value.

7 Claims, 5 Drawing Sheets

(51) Int. Cl.
*A61B 1/05* (2006.01)
*A61B 1/06* (2006.01)
*A61B 5/00* (2006.01)
*A61B 5/01* (2006.01)

(58) Field of Classification Search
CPC ........... A61B 2018/00809; A61B 2018/00815; A61B 2018/00821; A61B 2018/00005–00047; A61B 5/0008; A61B 5/01; A61B 2018/00011; A61B 2018/00017; A61B 2018/00023; A61B 2018/00029; A61B 2018/00041; A61B 2018/00047; A61B 18/02; A61B 18/04; H04N 5/33
See application file for complete search history.

(56) References Cited

U.S. PATENT DOCUMENTS

| | | | |
|---|---|---|---|
| 8,864,669 B2 | 10/2014 | Behar | |
| 2001/0047136 A1* | 11/2001 | Domanik | A61B 5/0071 600/473 |
| 2010/0191142 A1* | 7/2010 | Paul | A61B 5/015 600/549 |
| 2011/0230942 A1* | 9/2011 | Herman | A61B 5/0059 607/96 |
| 2014/0276091 A1 | 9/2014 | Angott et al. | |
| 2016/0249811 A1* | 9/2016 | Khan | A61B 1/00009 600/474 |
| 2017/0007310 A1* | 1/2017 | Rajagopalan | A61F 5/0079 |
| 2017/0027450 A1* | 2/2017 | Toledano | A61B 5/01 |

\* cited by examiner

ENDOSCOPE DEVICE FOR DETECTING DISEASE BASED ON THERMAL IMAGES

CROSS-REFERENCE TO RELATED APPLICATIONS

This application claims priority to Korean Patent Application No. 10-2016-0112819 filed on 2016-09-01 in Korea, the entire contents of which is hereby incorporated by reference in its entirety.

BACKGROUND

The present invention relates to an endoscope device. In detail, the present invention relates to an endoscope device that can diagnose a tumor in an early stage.

An endoscope, which is a device for visually examining the inside of a body, is necessary equipment under the modern medical environment because it can observe the inside with minimum invasiveness close to a non-invasive type. Such an endoscope allows for visually examining the inside of a body from the outside of the body, using a light source, optical fibers, and a camera that are generally used in the art.

Various studies for diagnosing and treating cancer that is at the top of causes of death in Korean in an early stage have been conducted. Imaging examination of the methods for diagnosing cancer in an early stage has a problem in that there is a possibility of radioactive exposure (CT, PET) and it takes a relatively long time to obtain images (for example, MRI). Further, the molecular imaging method that has been spotlighted needs to inject a fluorescence dye or a targeting probe into a human body, but probes that are available for a human body are limited. Further, the molecular imaging method gives mental stress to a patient and requires additional medical manpower and a reaction test from a patient.

Further, there is a thermal imaging method using body heat as a label-free diagnosis method. This method obtains images using the phenomenon that a fine difference is generated in heat of a human body between a neighboring tissue and a cancer tissue, but it simply images only the temperature difference, so the contrast of images is low.

SUMMARY

An embodiment of the present invention proposes an endoscope that can diagnose internal/external disease of a body without a hurt using kinetic thermal contrast imaging for diagnosing a tumor.

In detail, the present invention proposes an endoscope that increases contrast by making data of fine differences of heat differences between a neighboring tissue and a tumor.

An endoscope device according to an embodiment of the present invention includes: a heating source that heats a diagnosis target tissue; a cooling source that cools the diagnosis target tissue; a sensing unit that measures temperature of the diagnosis target tissue; and an image processing unit that obtains a first value meaning a temperature change for a predetermined time of the diagnosis target tissue heated by the heating source on the basis of the temperature obtained by the sensing unit, obtains a second value meaning time until the heated diagnosis target tissue is stabilized by being cooled by the cooling source after obtaining the first value, and produces an image for diagnose a tumor in the diagnosis target tissue on the basis of the first value and the second value.

The endoscope device according to an embodiment of the present invention can diagnose internal/external disease of a body without a hurt using kinetic thermal contrast imaging for diagnosing a tumor.

Further, the endoscope device according to an embodiment of the present invention provides a quantitative diagnosis, whereby it is possible to increase accuracy in tumor diagnosis.

BRIEF DESCRIPTION OF THE DRAWINGS

The present invention will become more fully understood from the detailed description given herein below and the accompanying drawings, which are given by illustration only, and thus are not limitative of the present invention, and wherein.

DETAILED DESCRIPTION OF THE EMBODIMENTS

Hereinafter, detailed embodiments of the present invention will be described in detail with reference to the accompanying drawings. However, the present invention is not limited to the detailed embodiments to be described below, other embodiments may be easily proposed by those skilled in the art by adding, changing, and removing components within the scope of the present invention, and those embodiments should be construed as being included in the scope of the present invention.

Figure 1:
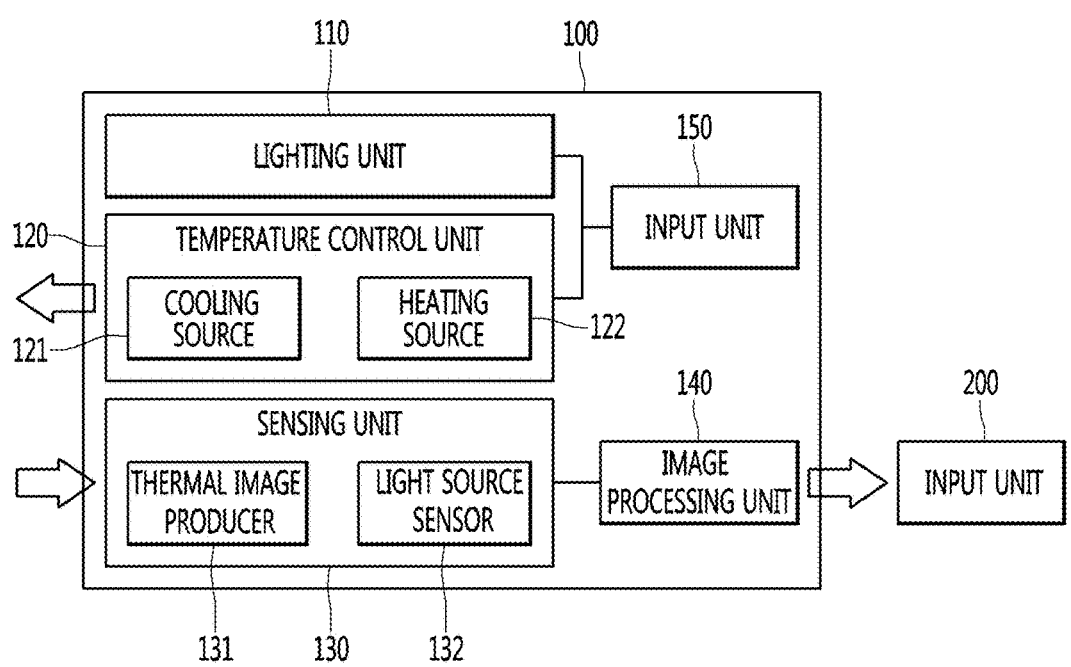
FIG. 1 is a block diagram schematically showing the configuration of an endoscope device according to an embodiment of the present invention.

FIG. 1 is a block diagram schematically showing the configuration of an endoscope device according to an embodiment of the present invention.

Referring to FIG. 1, an endoscope device 100 according to an embodiment of the present invention may include a lighting unit 110, a temperature control unit 120, a sensing unit 130, an image processing unit 140, and an input unit 150.

The lighting unit 110 can selectively provide narrowband light having a plurality of relatively narrow bands and white light having a relatively broad band. In detail, the lighting unit 100 may include a white light source that can emit white light having a relatively broad band including a near infrared band. For example, the white light source may be a Xenon lamp. Further, the lighting unit 110 may include a visible light filter that passes the visible light and a narrowband filter that passes narrowband light having different wavebands. The visible light filter passes only visible light having a wavelength of about 400~700 nm. Accordingly, light that is emitted from the white light source and passes through the visible light filter becomes pure while visible light.

The narrowband filter can pass only narrowband light having bands, for example, of blue, green, and near infrared. For example, the narrowband filter can pass only light having a relatively narrow blue wavelength band of 400~450 nm, a relatively narrow green wavelength band of 500~560 nm, and a relatively narrow near infrared wavelength band of 800~860 nm. Accordingly, the light that is emitted from the white light source and passes through the narrowband filter becomes narrowband blue light, narrowband green light, and narrowband light mixed with narrowband near infrared light. However, the passing bands are just examples and the detailed bands that the narrowband filter passes may be different, depending on embodiments.

The temperature control unit 120 may include a cooling source 121 and a heating source 122. The temperature control unit 120 can change the temperature of a diagnosis target tissue. The diagnosis target tissue means a predetermined area for tumor diagnosis in a body. The diagnosis target tissue may include a tumor. The diagnosis target tissue may be a predetermined area having a high possibility of including a tumor in a body. The size of the diagnosis target tissue may depend on the capacity of an endoscope device.

In detail, the cooling source 121 can decrease the temperature of a diagnosis target tissue. For example, the cooling source 121 can decrease the temperature of a diagnosis target tissue by emitting gas having temperature lower than body temperature to the diagnosis target tissue. The gas may be carbon dioxide or air.

Alternatively, the cooling source 121 can decrease the temperature of a diagnosis target tissue by emitting liquid having temperature lower than body temperature to the diagnosis target tissue. The liquid may be saline solution.

The heating source 122 can increase the temperature of a diagnosis target tissue. For example, the heating source 122 can increase the temperature of a diagnosis target tissue by emitting gas having temperature higher than body temperature to the diagnosis target tissue. The gas may be carbon dioxide or air. Alternatively, the heating source 122 can increase the temperature of a diagnosis target tissue by emitting liquid having temperature higher than body temperature to the diagnosis target tissue. The liquid may be saline solution. Alternatively, the heating source 122 may be radiant light. The radiant light may be the radiant light that is produced by a lamp.

The heating source 122 may include a visible light lamp or an infrared light lamp. The visible light lamp may be used to increase the temperature of blood in a body. The infrared light lamp may be used to increase the temperature of liquid that is used as a heating source.

The sensing unit 130 may include a thermal image producer 131 and a light source sensor 132. In detail, the thermal image producer 131 may include a thermal sensor. Further, the thermal image producer 131 may include a thermal image sensor or an IR fiber bundle. The light source sensor 131 may include an optical sensor.

The thermal image producer 131 can produce data for sensing a temperature change of a diagnosis target tissue. In detail, the thermal image producer 131 can produce a thermal image showing temperature distribution of a diagnosis target tissue. The produced image may be a 2D image showing temperature distribution at a predetermined time of the diagnosis target tissue.

For example, the heating source 122 can emit air having relatively high temperature to a diagnosis target tissue. The thermal image producer 131 can produce images of temperature distribution of a diagnosis target tissue at each predetermined time. In detail, the thermal image producer 131 can sense the temperature of each part of a diagnosis target tissue and produce a thermal image on the basis of the sensed temperature. The produced thermal image can be transmitted to the image processing unit 140 to be used for producing an image for disease diagnosis.

The light source sensor 132 can sense refractive light from a diagnosis target tissue to produce an image signal for the part irradiated in a body. To this end, the light source sensor 132 may include a plurality of light detection pixels arranged in a 2D array. One of the light detection pixels of the light source sensor 132 may include, for example, a near infrared sub-pixel for sensing near infrared light, a red sub-pixel for sensing red light, a blue sub-pixel for sensing blue light, and a green sub-pixel for sensing green light. Accordingly, the light source sensor 132 according to an embodiment of the present invention can sense even infrared light using a specific near infrared sub-pixel. Further, for example, a normal CMOD image sensor or CCD image sensor may be used to as a photosensitive device for the sub-pixels. In particular, an image sensor having a back-side illumination structure may be used to improve sensitivity for narrowband light.

An IR cut filter may be further disposed on the red sub-pixel, the blue sub-pixel, and the green sub-pixel to prevent influence on the red sub-pixel, the blue sub-pixel, and the green sub-pixel by near infrared light.

The image processing unit 140 can produce an image on the basis of the resultant value received from the sensing unit 130. For example, the image processing unit 140 can produce an image by mixing white visible light and narrowband light obtained from the light source sensor 132. Further, the image processing unit 140 can produce an image on the basis of a thermal image obtained from the thermal image producer 131. For example, the image processing unit 140 can produce an image from which it is possible to determine distribution of tumor tissues in a diagnosis target tissue by combining thermal images obtained for a predetermined time.

An image processed by the image processing unit 140 can transmitted to a display 200 to be shown to a user. The display 200 may be a separate device from the endoscope device 100. The display 200 may be a part of the endoscope device 100.

The input unit 150 receives input for controlling the endoscope device 100 from a user. For example, the input unit 150 may be a joystick for controlling the endoscope device 100. Alternatively, the input unit 150 may be a touch screen. The input unit 150 may provide an enlarged image for fine adjustment to a user.

A user can operate the endoscope device 100 through the input unit 150. In detail, a user can control the operation of the lighting unit 110 and the temperature control unit 120 through the input unit 150. For example, the input unit 150 can receive input for adjusting the intensity of the lighting unit 110. Further, the input unit 150 can receive input for operating the cooling source of the temperature control unit.

The operation of the lighting unit 110, temperature control unit 120, sensing unit 130, image processing unit 140, and input unit 150 can be controlled by control signals generated by a control unit (not shown). The control unit may be a system-on-chip in which various semiconductor devices are integrated.

Figure 2:
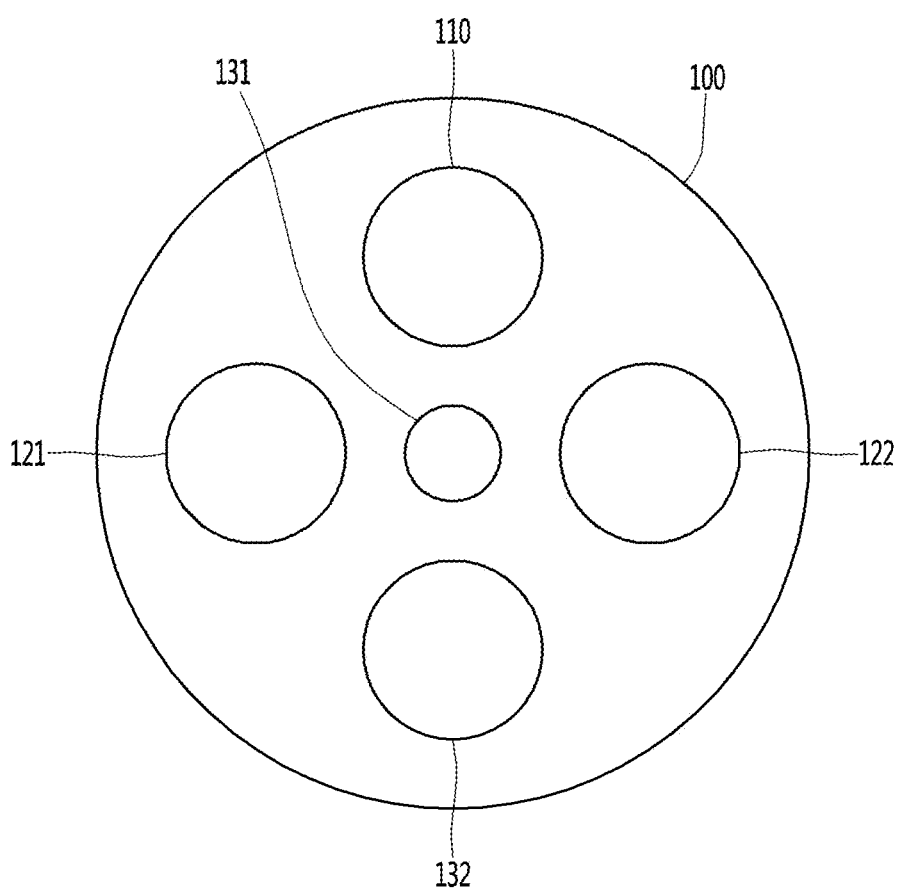
FIG. 2 is a view showing the front of the endoscope device according to an embodiment of the present invention.

FIG. 2 is a view showing the front of the endoscope device according to an embodiment of the present invention.

The positions of the components on the front of the endoscope device 100 shown in FIG. 2 may depend on embodiments. Further, unlike the configuration shown in FIG. 2, the components may be not independently positioned, but integrated.

Figure 3:
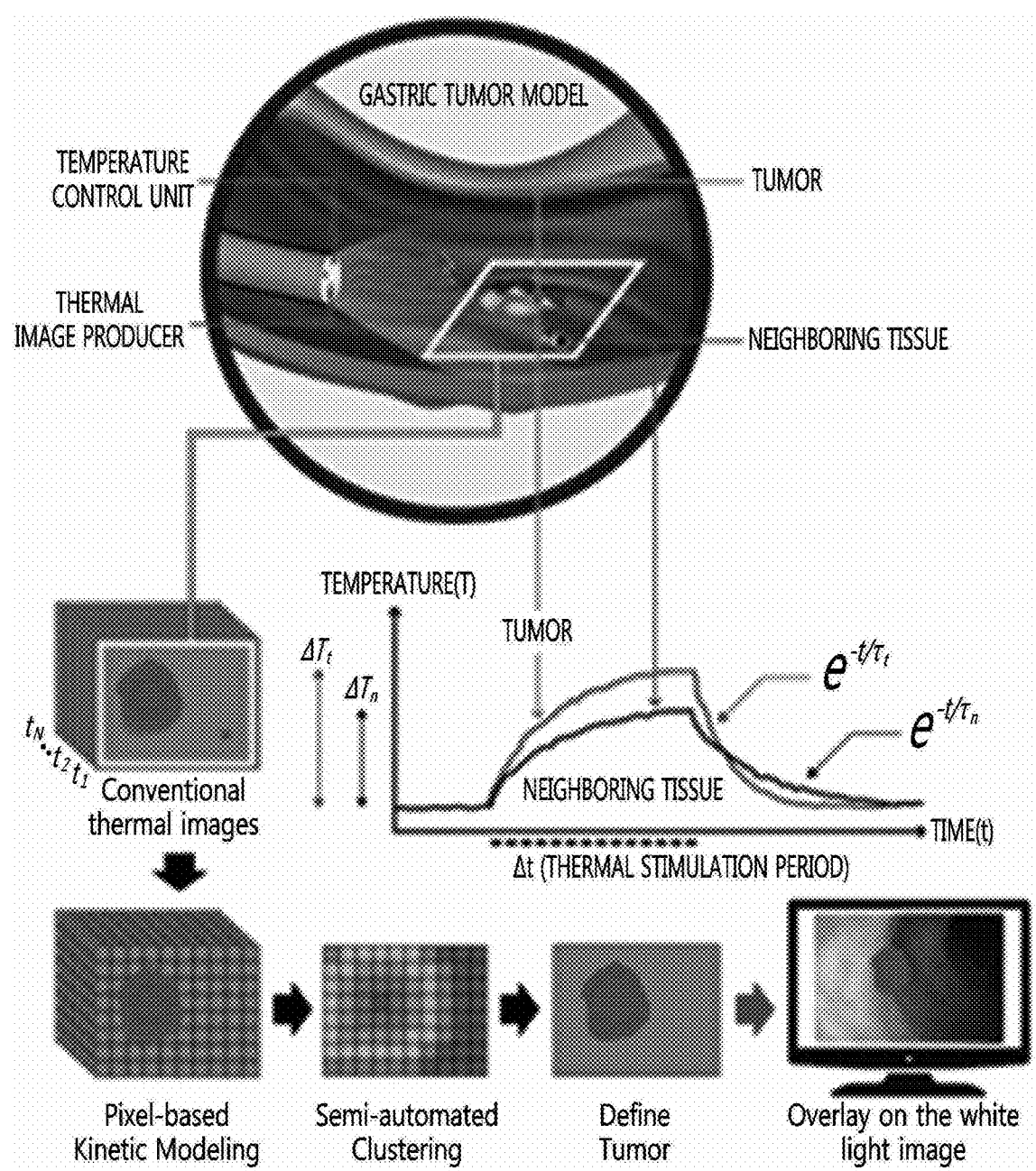
FIG. 3 is a view schematically showing a tumor diagnosis method using the endoscope device according to an embodiment of the present invention.

FIG. 3 is a view schematically showing a tumor tissue diagnosis method using the endoscope device according to an embodiment of the present invention.

As shown in FIG. 3, the endoscope device 100 applies a physiological change to a diagnosis target tissue including a tumor tissue and neighboring tissue. The endoscope device 100 measures first body temperature, applies a physiological change through the temperature control unit 120, and then measure again body temperature.

Further, the image processing unit 140 produces an image on the basis of a thermal image obtained from the thermal image producer 131. In detail, the image processing unit 140 produces an image on the basis of the range of the value of a physiological change. The image processing unit 140 can set the part having the largest physiological change as the center of a tissue. Further, the image processing unit 140 can determine a part having a physiological change larger than a reference value as a tumor by comparing physiological changes with the reference value and then image the tumor. Further, when a part has a physiological change larger than the reference value, the image processing unit 140 can determine the part as a normal tissue and image the normal tissue.

FIGS. 4A to 6 are views illustrating a diagnosis principle according to an embodiment of the present invention.

Figure 4A:
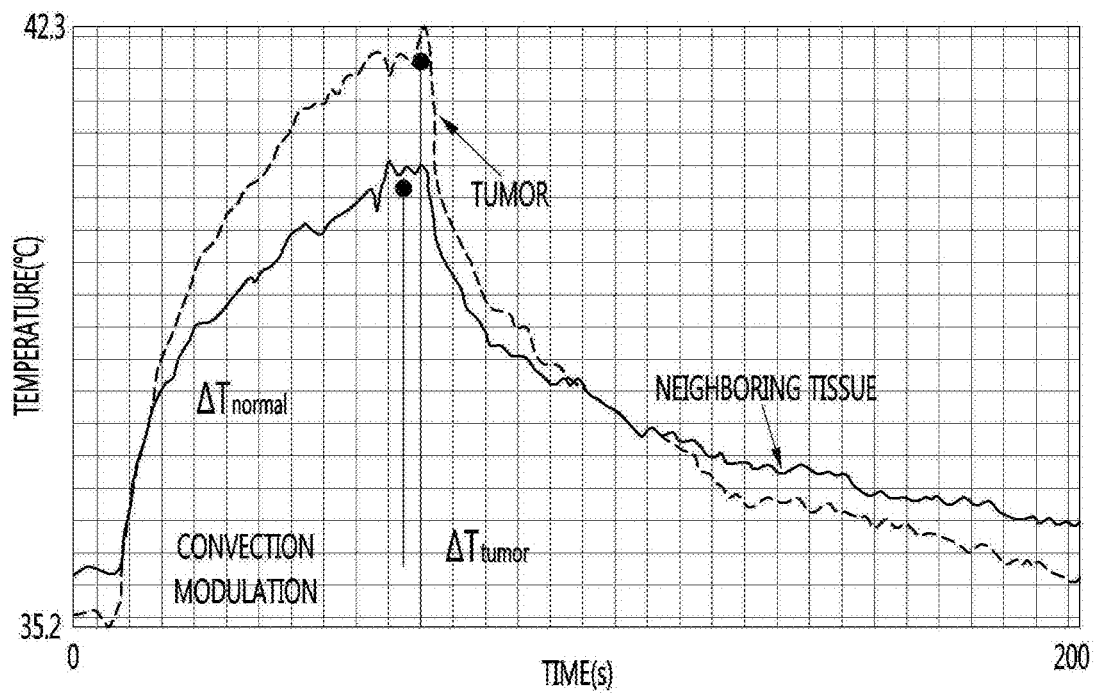
FIGS. 4A and 4B are views showing a temperature change between a tumor and a neighboring tissue during heating and cooling.
Figure 4B:
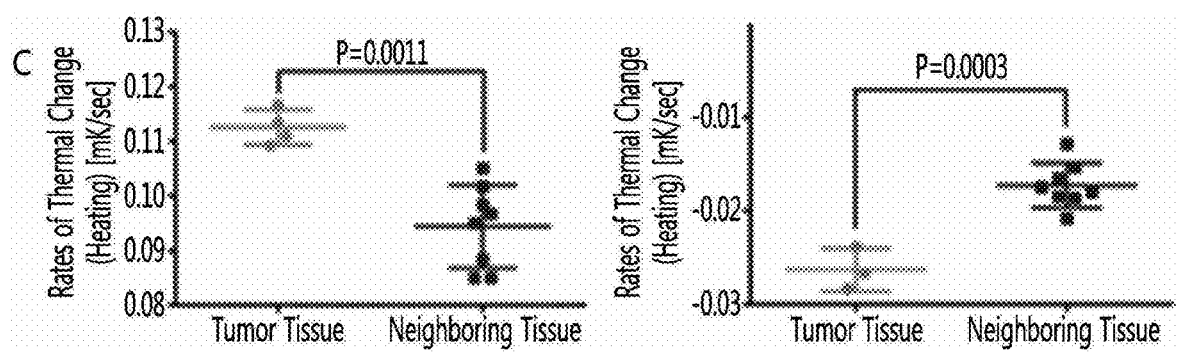

FIGS. 4A and 4B are views showing a temperature change between a tumor and a neighboring tissue during heating and cooling.

FIG. 4A is a graph constructed on the basis of a physiological change actually measured from a tumor and a neighboring tissue. FIG. 4B is another graph constructed on the basis of a physiological change actually measured from a tumor and a neighboring tissue.

A tumor tissue takes normal blood vessels going to normal tissues and takes components necessary for growth from the blood vessels. However, blood vessels do not normally growth in a tumor tissue, unlike normal tissues. Accordingly, a tumor tissue shows a large temperature change according to the external environment, unlike normal tissues. In detail, blood vessels pass through a normal tissue and the blood in the blood vessels has large specific heat, so a temperature change according to the external environment is relatively small in the normal tissue. However, in a tumor tissue, blood vessels do not normally grow, as described above, so most tumor tissues have relatively small specific heat as compared with blood. Accordingly, a tumor tissue shows a large temperature change according to the external environment, as compared with a normal tissue. In other words, it may mean that thermal capacitances of a tumor tissue and normal tissue are different. In detail, a tumor tissue has a small thermal capacitance and a normal tissue has a relatively large thermal capacitance.

Figure 5:
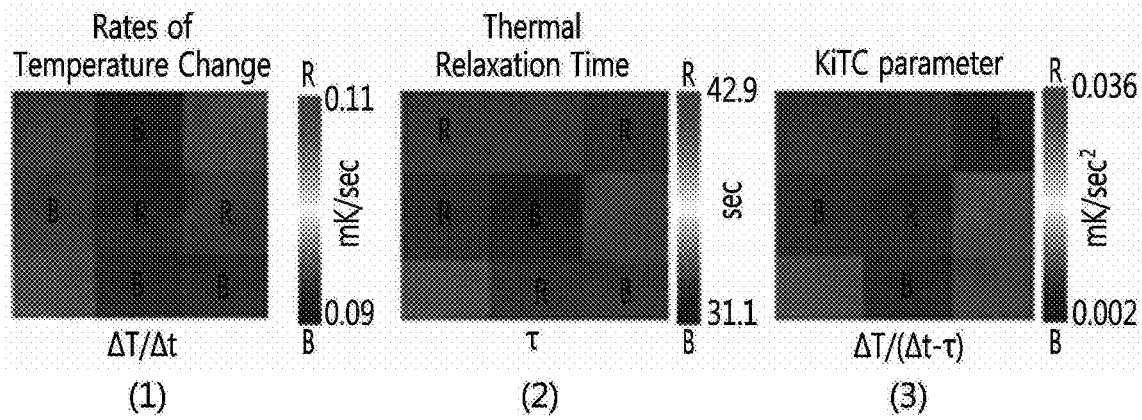
FIG. 5 is a view illustrating an improved tumor diagnosis method using a thermal image according to an embodiment of the present invention.

FIG. 5 is a view illustrating an improved tumor diagnosis method using a thermal image according to an embodiment of the present invention.

The thermal image shown in FIG. 5 has been produced by the image processing unit 140. In detail, the thermal image shown in FIG. 5 can be produced by combining thermal images produced by the thermal image producer 131 for a predetermined time.

The graph shown in FIG. 5 is divided as the following sections for easy description.

| 1 | 2 | 3 |
| 4 | 5 | 6 |
| 7 | 8 | 9 |

FIG. 5 shows three graphs. The first graph shows a temperature increase for a predetermined time when a normal tissue and a tumor tissue are heated. The second graph shows temperature stabilization time when the normal tissue and the tumor tissue are cooled. The third graph shows kinetic thermal contrast values of a normal tissue and a tumor tissue according to an embodiment of the present invention.

The first graph shows a temperature change for a predetermined time of a diagnosis target tissue according to operation of the heating source 122 of the endoscope device 100 according to an embodiment of the present invention. The temperature change for a predetermined time can be expressed as $\Delta T/\Delta t$.

As shown in the first graph, temperature changes by heating are different at each part in the diagnosis target tissue. In detail, referring to the first graph, the fifth and sixth sections show a large temperature change for a predetermined time. Therefore, according to the first graph, the endoscope device 100 can determine the fifth and sixth sections as tumor tissues. However, the difference is small (the difference between the maximum and the minimum is 0.02), so it may not be accurate to determine the parts as tumor tissues.

Accordingly, in order to solve this problem, the endoscope device 100 according to an embodiment of the present invention uses the second and third graphs to more accurately diagnose tumor tissues.

The second graph shows temperature stabilization time of a diagnosis target tissue according to operation of the cooling source 121 of the endoscope device 100 according to an embodiment of the present invention. The temperature stabilization time can be expressed by $\tau$.

As shown in the second graph, a tumor tissue and a normal tissue have different temperature stabilization times when they are cooled. In detail, referring to the second graph, it can be seen that the tissues in the fifth and ninth sections take the longest time to stabilize the temperature. The stabilization time means the time that temperature that has increased takes to be maintained at a predetermined level in accordance with homeostasis that a tissue returns to original temperature. As described above, a tumor tissue has a smaller thermal capacitance, as compared with a normal tissue, so it takes a short time to stability temperature.

The third graph shows values obtained by dividing a temperature change for a predetermined time obtained from the first graph by the stabilization time obtained from the second graph. The value obtained by dividing a temperature change for a predetermined time ($\Delta T/\Delta t$) by the stabilization time ($\tau$) can be referred to as kinetic thermal contrast (KiTC). The kinetic thermal contrast is a parameter obtained by considering all of a temperature change by the heating source and temperature stabilization time by the cooling source. Accordingly, the kinetic thermal contrast can increase image contrast between a normal tissue and a tumor tissue higher than an existing temperature increase for a predetermined time.

Therefore, according to an embodiment of the present invention, it is possible to more quickly and accurately determine the position of a tumor tissue on the basis of the increased image contrast. Further, the image processing unit 140 produces an image using kinetic thermal contrast having high image contrast, so it is possible to provide a relatively accurate position of a tumor to a user.

Figure 6:
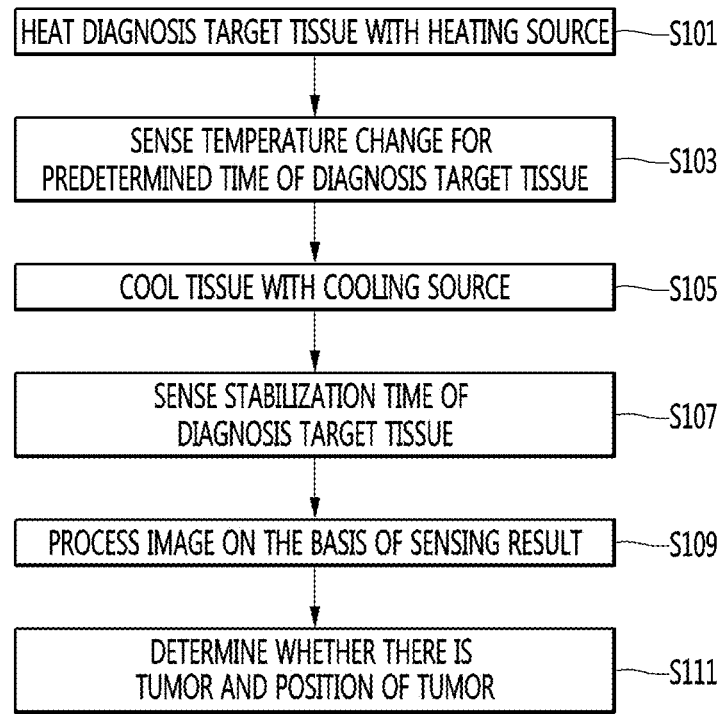
FIG. 6 is a flowchart illustrating the operation of the endoscope device according to an embodiment of the present invention.

FIG. 6 is a flowchart illustrating the operation of the endoscope device according to an embodiment of the present invention.

The endoscope device 100 is inserted into a body for diagnosis. When the inserted endoscope device 100 approaches a diagnosis target tissue, the following operation is performed.

The heating source 122 heats the diagnosis target tissue (S101). In detail, the heating source 122 performs heating on the basis of user input received from the input unit 150. For example, the heating source 122 may heat the diagnosis target tissue by emitting air at higher temperature than the body temperature.

The image processing unit 140 senses a temperature change of the diagnosis target tissue for a predetermined time (S103). In detail, the thermal image producer 131 may measure temperature distribution in the diagnosis target tissue and produce an image before heating, and measure temperature distribution in the diagnosis target tissue and produce an image after heating for a predetermined time. Further, the thermal image producer 131 can continuously produce images of the temperature distribution of the diagnosis target tissue at predetermined intervals.

The image processing unit 140 can obtain a plurality of thermal images from the thermal image producer 131. The image processing unit 140 can obtain a first value. The first value may be a temperature change (mK/sec) for a predetermined time. The image processing unit 140 can obtain the first value on the basis of the thermal images obtained from the thermal image producer 131 and the measuring time. The image processing unit 140 can image the first value (for example (1) in FIG. 5).

When the image processing unit 140 obtains the first value, the cooling source 121 cools the diagnosis target tissue (S105). In detail, the cooling source 121 performs cooling on the basis of user input received from the input unit 150. For example, the cooling source 121 may cool the diagnosis target tissue by emitting air at lower temperature than the body temperature. Alternatively, the cooling source 121 may cool the diagnosis target tissue by emitting water at lower temperature than the body temperature.

The image processing unit 140 senses whether the temperature of the diagnosis target tissue is stabilized (S107). In detail, it measures the time when the temperature of the diagnosis target tissue is stabilized after the first value is obtained. The temperature of the diagnosis target tissue can be obtained from the thermal image producer 131. In detail, the image processing unit 140 can obtain a thermal image obtained by imaging the temperature distribution of the diagnosis target tissue from the thermal image producer 131.

The case when the temperature of the diagnosis target tissue is stabilized means the case when the heated diagnosis target tissue is cooled and has only a small temperature change within a predetermined range. For example, when the distribution of temperature of the diagnosis target tissue measured at each time has a change of 1 second or more and 0.1 degrees of less, the image processing unit 140 can determine that the diagnosis target tissue has entered stabilization. In other words, the case when the diagnosis target tissue is stabilized means that the body restores homeostasis. When the temperature is stabilized, the temperature of the diagnosis target tissue may be the body temperature.

The temperature stabilization time means time that is taken until the heated diagnosis target tissue recovers to the normal temperature for maintaining homeostasis and shows a stable temperature change. The time for temperature stabilization may be referred to as a second value. Meanwhile, the image processing unit 140 can obtain the second value from the thermal image of the diagnosis target tissue obtained from the thermal image producer 131. In detail, the image processing unit 140 can determine the time taken until the diagnosis target tissue is stabilized after the first value is obtained, as the second value. The second value can be imaged by the image processing unit (for example, (2) in FIG. 5).

The image processing unit 140 processes an image on the basis of a sensing result that the thermal image producer 131 has obtained (109). In detail, the image processing unit 140 produces an image for determining a tumor tissue on the basis of a thermal image transmitted from the thermal image producer 131.

In an embodiment of the present invention, the image processing unit 140 can obtain the kinetic thermal contrast (KiTC) for the entire diagnosis target tissue on the basis of the first and second values. The kinetic thermal contrast can be obtained by dividing the first value by the second value. The image processing unit 140 can produce an image on the basis of the KiTC. In detail, the image processing unit 140 can produce an image with different colors in accordance with the KiTC (fore example, (3) in FIG. 5). The image processing unit 140 can provide the produced image to a user by transmitting the image to the display 200.

The image processing unit 140 determines whether there is a tumor and the position of a tumor when there is a tumor on the basis of the KiTC (S111). In detail, the image processing unit 140 can compare the KiTC with a predetermined reference value and determine a part where the KiTC is larger than the reference value as a tumor tissue and a part where the KiTC is smaller than the reference value as a normal tissue. The reference value for the determination may depend on the condition of the patient.

As a result, the endoscope device according to an embodiment of the present invention uses not only a thermal change due to heating, but KiTC considering the stabilization time by cooling in order to diagnose a tumor tissue, whereby it is possible to more quickly and accurately diagnose a tumor, as compared with existing methods.

An endoscope device and a method of diagnosing a tumor using an endoscope device was exemplified and shown in the drawings to help understand the present invention. However, it should be understood that the embodiments are just examples of the present invention and the present invention is not limited thereto. Further, it should be understood that the present invention is not limited to the above description and the drawings. This is because the present invention may be modified in various ways by those skilled in the art.

What is claimed is:

1. An endoscope device configured to be inserted into a body to diagnose a tumor tissue, the endoscope device comprising:
 a heating source that heats a diagnosis target tissue;
 a cooling source that cools the diagnosis target tissue;
 a sensing unit that produces a thermal image by measuring temperature distribution of the diagnosis target tissue; and
 an image processing unit configured to:
  obtain a first value meaning a rate of temperature change of the diagnosis target tissue heated by the heating source on the basis of the thermal image obtained by the sensing unit, obtain a second value meaning time until the heated diagnosis target tissue is stabilized by being cooled by the cooling source after obtaining the first value, and produce an image for diagnosing the tumor tissue in the diagnosis target tissue on the basis of the first value and the second value, wherein the heated diagnosis target tissue is stabilized when the heated diagnosis target tissue is cooled and has a temperature change within a predetermined range, and wherein the image processing unit is controlled by a system-on-chip, and is further configured to obtain:

a third value by dividing the first value by the second value, compare the third value with a predetermined reference value and produce the image showing a part having the third value larger than the reference value in the diagnosis target tissue as the tumor tissue.

2. The endoscope device of claim 1, further comprising a display that displays the image produced by the image processing unit.

3. The endoscope device of claim 1, wherein the heating source heats the diagnosis target tissue by emitting one of gas, liquid, and radiant light at higher temperature than body temperature.

4. The endoscope device of claim 3, wherein the liquid is saline solution, the gas is carbon dioxide or air, and the radiant light is generated by a lamp.

5. The endoscope device of claim 1, wherein the cooling source cools the diagnosis target tissue by emitting one of gas and liquid at lower temperature than body temperature.

6. The endoscope device of claim 5, wherein the gas is air or carbon dioxide and the liquid is saline solution.

7. A method of operating an endoscope device configured to be inserted into a body to diagnose a tumor tissue, the method comprising:

heating a diagnosis target tissue;

obtaining a first value meaning a rate of temperature change of the diagnosis target tissue;

cooling the heated diagnosis target tissue;

obtaining a second value meaning time until the heated diagnosis target tissue is stabilized by being cooled after the first value is obtained; and producing an image for diagnosing the tumor tissue in the diagnosis target tissue on the basis of the first value and the second value, wherein the heated diagnosis target tissue is stabilized when the heated diagnosis target tissue is cooled and has a temperature change within a predetermined range, and wherein the producing of the image for diagnosing the tumor tissue includes:

obtaining a third value by dividing the first value by the second value;

comparing the third value with a predetermined reference value; and producing the image showing a part having the third value larger than the reference value in the diagnosis target tissue as the tumor tissue.

* * * * *